United States Patent
Waddell et al.

(10) Patent No.: US 6,712,799 B2
(45) Date of Patent: Mar. 30, 2004

(54) DISPOSABLE WATER SEAL FOR THORACIC REGULATORS

(75) Inventors: Paula M. Waddell, Baltimore, MD (US); Thomas C. Jones, Columbia, MD (US)

(73) Assignee: Datex-Ohmada, Inc., Madison, WI (US)

(*) Notice: Subject to any disclaimer, the term of this patent is extended or adjusted under 35 U.S.C. 154(b) by 91 days.

(21) Appl. No.: 09/994,538

(22) Filed: Nov. 27, 2001

(65) Prior Publication Data

US 2003/0100890 A1 May 29, 2003

(51) Int. Cl.[7] .............................................. A61M 1/00
(52) U.S. Cl. ............................................................ 604/321
(58) Field of Search ............................... 604/318–321, 604/322, 323, 326, 327, 541

(56) References Cited

U.S. PATENT DOCUMENTS

| | | | |
|---|---|---|---|
| 3,279,467 A | | 10/1966 | Hofstra et al. |
| 3,363,626 A | | 1/1968 | Bidwell et al. |
| 3,625,216 A | * | 12/1971 | Pannier et al. ............... 604/321 |
| 3,847,152 A | * | 11/1974 | Schachet ..................... 604/321 |
| 3,946,735 A | | 3/1976 | DeWall |
| 4,266,765 A | * | 5/1981 | Sandoval et al. ...... 280/47.371 |
| 4,289,158 A | | 9/1981 | Nehring |
| 4,439,190 A | * | 3/1984 | Protzmann et al. ......... 137/205 |
| 4,650,477 A | | 3/1987 | Johnson |
| 4,655,242 A | | 4/1987 | Hamazaki et al. |
| 4,747,843 A | * | 5/1988 | Felix et al. .................. 604/318 |
| 4,769,019 A | * | 9/1988 | Kerwin ........................ 137/205 |
| 5,419,769 A | | 5/1995 | Devlin et al. |
| 5,527,007 A | | 6/1996 | Weilbacher |

FOREIGN PATENT DOCUMENTS

| | | |
|---|---|---|
| CH | 345 421 | 3/1960 |
| EP | 0 111 087 | 6/1984 |

OTHER PUBLICATIONS

Chest Tubes, pp. 46–55, Dec. 1995, RN Magazine.
Rereptaseal® Thoracic Manometer (date unknown) pp. 1–29.

* cited by examiner

Primary Examiner—Weilun Lo
Assistant Examiner—Michael Bogart
(74) Attorney, Agent, or Firm—Roger M. Rathbun

(57) ABSTRACT

A thoracic drainage system for removing liquid from the thoracic cavity of a patient. The system includes a reusable thoracic vacuum regulator and a standard disposable collection container. A disposable water seal chamber is also provided that can be disposed of after each patient and is a separable, independent component. There is also a combination thoracic vacuum regulator having a water seal chamber removable affixed thereto to enable the water seal chamber to be readily removed from the thoracic vacuum chamber in order to carry the water seal chamber along with the patient as that patient is transported.

19 Claims, 4 Drawing Sheets

DISPOSABLE WATER SEAL FOR THORACIC REGULATORS

BACKGROUND

The present invention relates to a system that can be used to withdraw liquids from a patient in a medical environment by a means of a chest tube, and, more particularly, to a thoracic drainage system having an improved, disposable component.

There are in use today, a considerable selection of thoracic drainage systems that carry out the withdrawal of liquids from a patient. In general, after many surgical operations, there is a need to remove certain liquids from a patient and, in particular, there is a need to remove fluids from the thoracic cavity of the patient. Such fluids build up after surgery and include secretions such as blood and plasma that accumulate and must therefore be removed from the patient to prevent such build up from becoming harmful to the patient.

Typically, such systems for the removal of the fluids comprise three basic components that are used in conjunction with the chest tube and the various tubes that are used to connect those components together and to a vacuum system within the hospital. First, fluids removed from the patient via a chest tube are collected in a collection chamber where those fluids are accumulated and the collection chamber is either periodically emptied or disposed of altogether. Next, there is a water seal that is used to prevent ambient air from reaching the chest cavity as well as to provide a visual indication to the caregiver of a possible leak in the overall thoracic drainage system. Lastly, there is a vacuum control that regulates the amount of vacuum that is applied to the system from the source of vacuum provided generally by the hospital central vacuum system or may be through the use of a localized vacuum source.

In the past, the various functions of the aforementioned components were carried out by the use of three individual bottles. One of the bottles collected the liquid from the patient, a second bottle provided the function of a water seal to prevent the back flow of ambient air into the chest cavity and third bottle acted like a regulator and comprised a water manometer having a fixed height of water such that when the vacuum exceeded a predetermined level, air would pass into the water manometer and limit the level of vacuum to the thoracic drainage system and ultimately, of course, to the patient cavity. By changing the level or height of the water, different maximum levels of vacuum could be attained.

The three bottle system, however, left a considerable number of parameters undecided and was sometimes difficult and tedious to set up properly by the user that had to be trained in the set up procedures. Accordingly, to counter those problems, various systems were devised that integrated all of the aforementioned three functions into a single apparatus. Thus, the usual apparatus today collectively incorporates a collection container or chamber, a water seal and a means of regulating the amount of vacuum to the overall system. An example of such apparatus is shown and described in U.S. Pat. No. 3,363,626 of Bidwell et al where a single, disposable underwater drainage unit is disclosed where a transparent plastic unit is provided to carry out all of the steps of a collection container, an underwater seal chamber and a water manometer incorporated therein and which eliminates the set up procedures used with the three bottle system and thus reduces the possibilities of an incorrect coupling or filling of the individual bottles. Thus, the emphasis of such systems is in the incorporation into a single apparatus, of all of the three functions of the normal thoracic drainage system, that is, the collection chamber, the water seal and water manometer Typical today of such systems is the Pleur-evac apparatus manufactured and marketed by Deknatel, Snowden, Pencer or DSP and the entire apparatus is constructed so as to be disposable and to integrate into a single apparatus, the functions of the water manometer, the water seal and the collection chamber. Other such apparatus are commercially marketed by Sherwood Medical and Baxter Healthcare and all are typical of the systems currently marketed for the drainage of the thoracic cavity and all incorporate the functions of a vacuum regulator, water seal and collection chamber into an integrated apparatus. With such integrated systems, however, the overall cost of the apparatus is still relatively high and it is not always cost effective to dispose of the entire apparatus after each patient. There is, in such systems a considerable expenditure of money that is totally lost after use on one patient. Even though easier to assemble and possibly less expensive than having three separate components for the three functions, the overall cost of an integrated apparatus still is quite substantial and it would be advantageous to have a thoracic drainage system serving the full functions of such a system but at a lesser cost to the hospital.

Accordingly, it would be advantageous to have a plural drainage apparatus or system that can employ, to the extent possible, standard components, such as, for example, the collection container since collection containers are readily available by themselves and are very inexpensive, as compared with an entire thoracic drainage apparatus and the disposal of a collection chamber can be very cost efficient to simply be discarded after its use with an individual patient. As such, it would be a cost savings to take advantage of the many collection chambers that are currently available in the marketplace from a number of companies that simply collect fluids for disposal and due to the high usage of such collection chambers, the cost of such containers is very low.

There is also available, an improved vacuum regulator that is specially adapted for use with thoracic drainage and which is marketed by Datex-Ohmeda, Inc, the present assignee, and which is capable of providing the precise levels and ranges of vacuum needed for thoracic drainage having the characteristics of relatively high flow and low impedance, i.e. a level of vacuum between a negative pressure of about 5 cm. water to about 50 cm. water and therefore is a reusable component that can be used with multiple patients and not disposed of after each use. By the use of such a regulator, that component can be used repetitively and the cost, therefore, not wasted after the use on a single patient.

In addition, it is advantage for the caregiver to continually visually monitor the water seal function of the apparatus as it provides an indication of the presence of a leak in the overall system. For example, if bubbles are continually being formed in the water seal component, it is generally an indication that there is an air leak into the system and the leak can thereafter be traced by occluding the drainage tubing at various locations to ascertain the location of that leak. However, with an integrated system, the collection chamber where the liquids from the patient are being collected must be located below the patient, or, more specifically, below the particular cavity that is being drained by the system, in order to prevent a siphoning effect that can return liquid accumulated in the collection chamber back to the patient. As such, the typical integrated apparatus must itself be located below the patient, generally on the floor of the patient room and thus it is quite inconvenient for the caregiver to be able to visually check the functioning of the water seal to ascertain and verify its proper operation. It would, obviously be more advantageous if the water seal component or function were located at a convenient height for the caregiver and preferable at the eye level of that caregiver.

Too, with the present integrated thoracic drainage systems, in the event it is necessary to move a patient from one location to another, the apparatus must, of course, be disconnected from the source of vacuum in order to make such movement. With the integrated apparatus, the apparatus itself is also normally disconnected as it is cumbersome to move that apparatus that includes various liquids within the collection chamber and the water manometer along with the patent, however, it is important that the water seal be maintained to insure that ambient air does not enter the patient cavity during the move. Accordingly, since it is so cumbersome to move the typical integrated apparatus containing liquid in the various chambers and containers, there is often a makeshift water seal that is assembled on site by the caregiver to place the patient tube into a container of water to keep the water seal function during the move. Obviously, such an arrangement is not particularly desirable as it is difficult to assemble the water seal and the movement can cause the makeshift water seal to spill or become disconnected from the patient.

It would, therefore, also be advantageous to be able to easily separate the water seal function from the other component or components so as to only maintain that water seal function for the protection of the patient in transit without involving the other components, that is, to continue the function of the water seal as the patient is in actual transit without also carrying along the collection container.

There is, therefore, clearly a need for some type of apparatus that can be used in a thoracic drainage system that provides accurate, safe drainage of the patient by means of a chest tube or the like and which can make use of a standard collection chamber or container that is cost effective so as to be disposable after each patient, a reusable vacuum regulator that can be used with a plurality of patients and a water seal component that can be a separate, inexpensive component that is fully cost effective as a disposable device but, additionally, can be located above the patient, preferable at the eye level of the caregiver so that it can be visually monitored easily and without inconvenience to that caregiver.

SUMMARY OF THE INVENTION

Accordingly, the present invention relates to a method and apparatus that is used in carrying out the thoracic drainage of a patient in a hospital environment. The present apparatus and method is used with a chest tube to drain the thoracic cavity of the patient and can be used with a standard collection container to accumulate the fluids drained from the patient. The vacuum is regulated and controlled to the desired level of vacuum by means of a reusable thoracic drainage regulator based on a construction that is presently available commercially to the market. As to the remaining components, a unique disposable water seal function is provided by having an inexpensive construction of a water seal that can be a separate component, pre-filled with a sterile liquid, and which is comprised of easily mass produced molded parts.

With the water seal component manufactured as a disposable, independent device, it can be seen that the water seal can therefore be located at any level with respect to the patient cavity being drained since the normal fluid collection container is a separate component and can be located at the desired level below the patient cavity being drained and yet the disposable water seal component can be at any elevated position above the patient and conveniently located at the eye level of the caregiver to improve the ability of that caregiver to continuously monitor the water seal and its functioning to verify that no leaks are occurring in the system.

In a further embodiment of the present invention, the disposable water seal component can be built into the housing of the thoracic vacuum regulator by a unique interlocking arrangement and thus the thoracic regulator and the water seal chamber can be manufactured and supplied as a single integrated unit, however, even then, the water seal chamber is adapted to be readily removable from the housing of the vacuum regulator and disposed of cost effectively. Again, therefore, with the combined water seal chamber and thoracic vacuum regulator embodiment, the water seal chamber can be located at the eye level of the caregiver since that location is the normal elevation of a vacuum regulator affixed to the central vacuum system of a hospital.

As a further feature of the built-in embodiment, since the water seal is easily detachable from the thoracic vacuum regulator, in the event it becomes necessary to move a patient, that water seal component can be detached from the housing combining it with the thoracic vacuum regulator and simply hung on a standard IV post that is normally on the bed or otherwise accompanying the patient during the move. As such, the water seal function can easily be continued as the patient is moved and yet there is no need to move the collection chamber or the remaining components that make up the thoracic vacuum system.

Additional features and advantages of the invention will become apparent to those skilled in the art upon consideration of the following detailed description of preferred embodiments exemplifying the best mode of carrying out the invention.

DETAILED DESCRIPTION OF THE INVENTION

Figure 1:
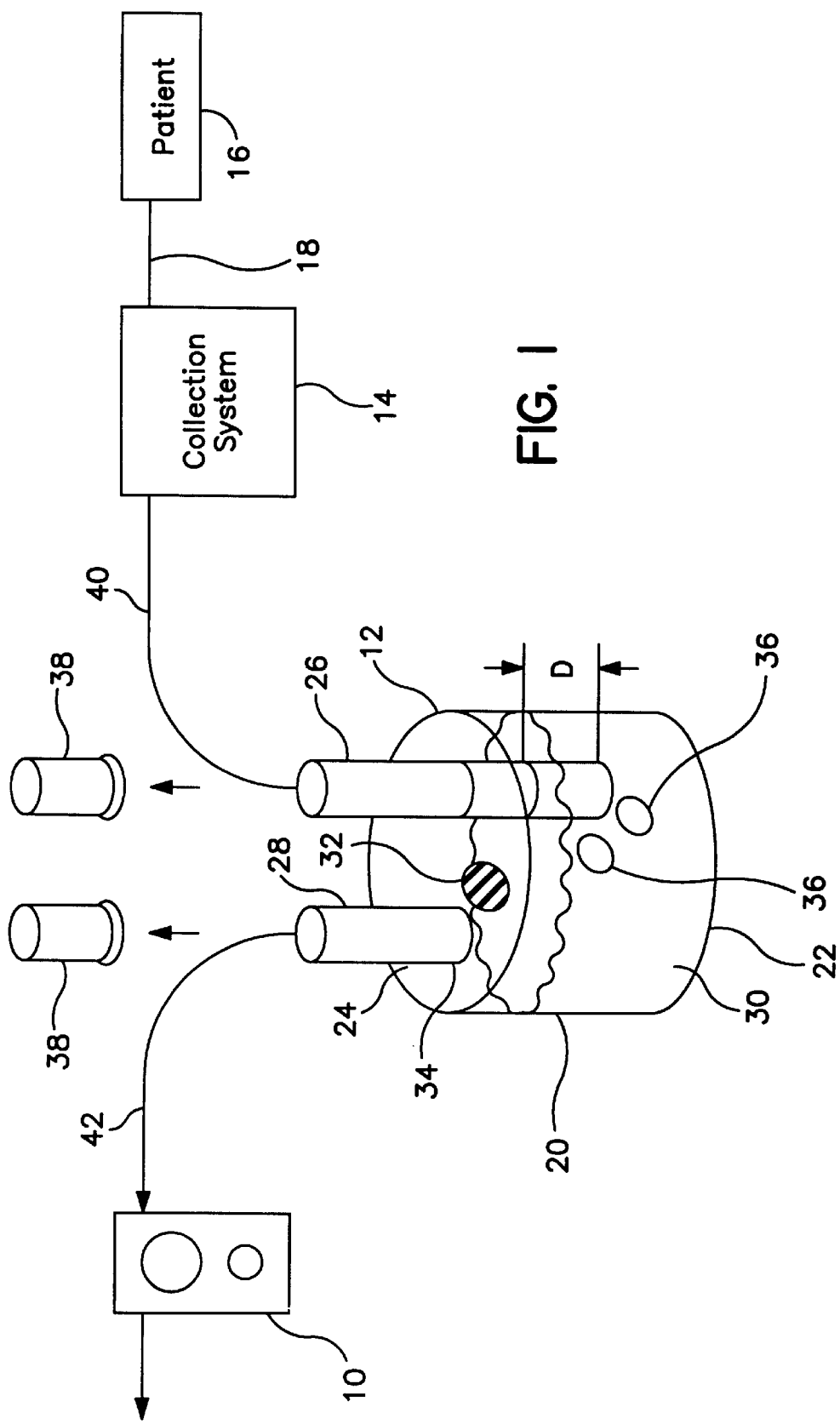
FIG. 1 is a schematic view of a thoracic drainage system utilizing a disposable water seal component constructed in accordance with the present invention.

Turning now to FIG. 1, there is shown a schematic view of the thoracic drainage system of the present invention. As can be seen, there is a vacuum regulator 10 that is adapted to be connected to a source of vacuum, generally, a central hospital vacuum source that is available within certain rooms within the hospital. Next, there is a water seal chamber 12 and a collection container 14. A patient, identified as 16, having a chest tube or other tube is connected to the collection container 14 by a suitable conduit 18. The collection container 14 is a standard disposable component that can be obtained from any number of suppliers and is sufficiently inexpensive so as to be economically disposable and mass produced for such use. In any event, the collection container 14, as will be seen, is used to collect and accumulate the liquid withdrawn from the thoracic cavity of the patient 16.

As used herein, the convention will be employed that follows the flow in the vacuum line, that is, the source of vacuum will be defined as a downstream location and the patient cavity at an upstream location and the terms upstream and downstream will be used with reference to the flow of fluid in the direction from the patient toward the source of vacuum.

The water seal chamber 12 is comprised of a transparent plastic material which is, therefore, relatively inexpensive to manufacture and thus can be made to be economically disposable after each use. The water seal chamber 12 is basically a closed chamber and is comprised of a cylindrical side 20, a bottom 22 and a cover 24. Affixed to the cover 24 are an inlet 26 and an outlet 28, both of which communicate with the interior of the closed chamber. There is contained within the water seal chamber 12 a quantity of a liquid 30, generally sterile water, that is used to carry out the normal function of a water seal.

In a preferred embodiment, the quantity of liquid 30 is pre-filled, that is, the manufacturer of the water seal chamber 12 can supply the water seal chamber 12 already filled with that liquid 30 contained therein and than quantity of liquid is a predetermined volume such that the inlet 26 extends below the level of that liquid a predetermined distance, generally 2 cm. In the cover 24 there is also a small opening 32 covered with a flexible diaphragm 34 and which can be used to insert a syringe to add additional liquid to the water seal chamber 12. In addition, since the water seal chamber 12 can be shipped pre-filled with the liquid, there are caps 38 that are used to seal off the open ends of both the inlet 26 and the outlet 28.

As such, in the normal course of providing a water seal function, the inlet 26 terminates within the water seal chamber 12 about 2 cm. below the level of the liquid therein and bubbles 36 can be seen that indicate a leak to the caregiver as will be later explained.

A suitable conduit 40 provides fluid communication between the collection container 14 and the inlet 26 of the water seal chamber 12 and a further suitable conduit 42 provides fluid communication between the outlet 28 of the water seal chamber 12 and the vacuum regulator 10. As stated, the vacuum regulator 10 is preferably a reusable vacuum regulator that is capable of providing negative pressure levels of from about 5.0 cm. water to about 50 cm. water and is of the type that has relatively high flow and low impedance. A suitable commercial thoracic vacuum regulator is available from Datex-Ohmeda, Inc of Laurel, Md. Thus, the thoracic vacuum regulator 10 is a commercially available component that is reusable and therefore can be utilized with a plurality of patients and need not be replaced after each use, thus contributing to the overall economics of the present invention.

According in the overall function of the thoracic drainage system of the present invention, the vacuum source powers the system and that vacuum at the vacuum source is regulated to the predetermined desired level by the vacuum regulator 10. The regulated vacuum level is ultimately applied to the thoracic cavity of the patient 16 to withdraw liquids from that cavity to enter and be collected in the collection container 14. The water seal chamber 12 is located downstream of the collection container 14 and provides the normal water seal function to prevent the ambient air from flowing backwardly into the patient cavity. In addition, one of the functions of the water seal chamber 12 is to alert the caregiver of the presence of a leak in the thoracic drainage system and, to that end, the caregiver can observe the bubbles 36 that are formed in the water seal chamber 12 upon the presence of a leak in the overall system.

Figure 2:
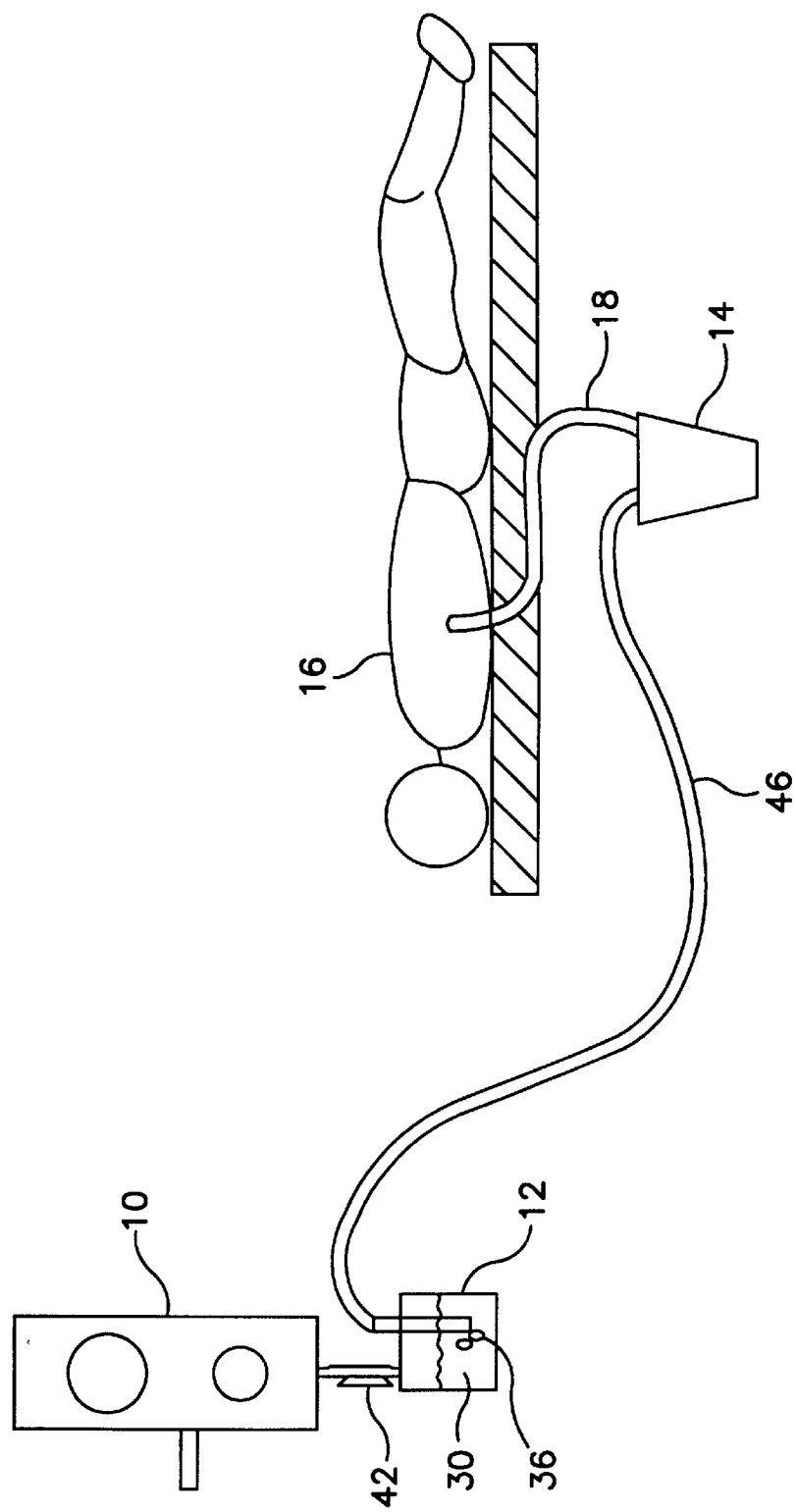
FIG. 2 is a schematic view of a thoracic drainage system of FIG. 1 showing the relative heights of the location of the components.

Turning now to FIG. 2, there is shown, a schematic view of the present thoracic drainage system with the components in the preferred locations. In this Figure, the relative location of the patient 16 is shown and also the location of the collection container 14 that is, as has been indicated, necessarily located below the patient cavity that is being drained by the system. With the present invention, however, instead of an integrated drainage system with all of the components in a unitary apparatus located beneath the level of the patient, since the water seal chamber 12 is a separable, disposable component, it can be located at or near the location of the thoracic vacuum regulator 10 so as to be at the eye level of the caregiver. As such the caregiver can easily monitor the water seal chamber 12 and immediately notice the formation of bubbles 36 without stooping to visually viewing the water seal container of a conventional integrated apparatus located on the floor of the patient's room.

Figure 3:
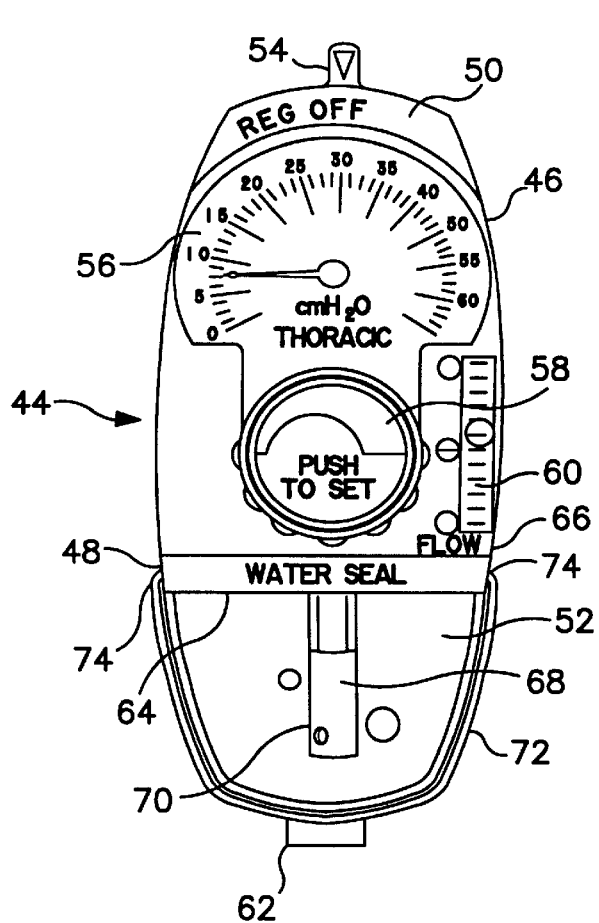
FIG. 3 is a front view of an embodiment comprising a combined water seal chamber and thoracic vacuum regulator.

Turning now to FIG. 3, there is shown a front view of a further embodiment of the present invention where there is shown a combination of a thoracic regulator and water seal chamber. In this embodiment, there is a common housing 44 having an upper portion 46 that contains the normal thoracic vacuum regulator 50 and a lower portion 48 that provides a receptacle for the water seal chamber 52 such that the water seal chamber 52 is removably affixed to the housing 44.

The components of the thoracic vacuum regulator 50 of this embodiment are basically the standard functions including an operating switch 54, a regulator gauge 56 in order for the caregiver to determine that the level of the negative pressure set by the vacuum regulator 50 and a knob 58 that allows the caregiver to set the desired level of vacuum established by the vacuum regulator 50. There may also be a flow indicator 60 to enable the caregiver to visually note a relative flow through the vacuum system.

Next, in the lower portion 48 of the housing 44, there is a water seal chamber 52 that has an inlet 62 that, of course, connects to a collection container 14 as shown in FIGS. 1 and 2. There is also an outlet, not shown in FIG. 3, that is formed in the upper surface 64 of the water seal chamber 52 and with interconnects with an inlet (not shown) in the lower surface 66 of the thoracic vacuum regulator 50. As will be seen, when the water seal chamber 52 is interconnected to the thoracic vacuum regulator 50 as shown in FIG. 3, the inlet to the thoracic vacuum regulator 50 and the outlet of the water seal chamber 52 are in communication with each other so that the regulated vacuum is applied to the water seal chamber 52 to draw the liquid from the patient as explained with reference to FIGS. 1 and 2.

As is also shown and described with respect to FIGS. 1 and 2, there are various passageways within the water seal chamber 52 so that the water seal inlet 62 communicates with the water seal chamber 52 at a point below the surface of the liquid 68 that is visible through a water glass 70 and the outlet of the water seal chamber is above the level of that liquid 68. Again, as in the prior embodiment there is generally a 2 cm. difference in the inlet location and the level of the liquid 68. As also seen in FIG. 3, there is a locking hanger 72 that is pivotally affixed to the water seal chamber 52 at points 74 and its purpose will be later explained.

There is an attachment means that interconnects the water seal chamber 52 to the housing 44 so that the water seal chamber 52 can be detached by the caregiver as desired. The actual means of removably affixing the water seal chamber 52 to the housing 44 can be by a variety of mechanism, it only being of importance that the attachment and removal be relatively easy and that the attachment aligns the inlet of the vacuum regulator 50 with the outlet of the water seal chamber 52 so that there is communication therebetween when the water seal chamber 52 is in its affixed position as shown in FIG. 3.

Figure 4:
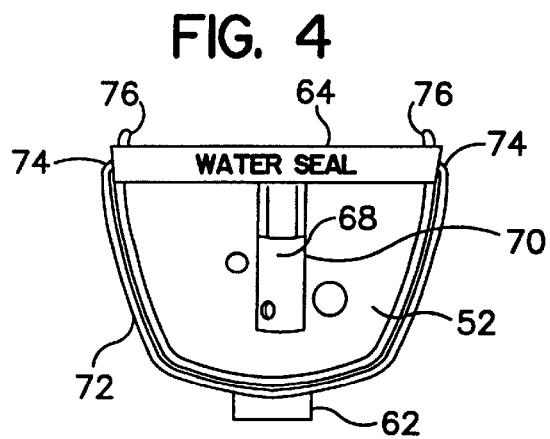
FIG. 4 is a front view of the water seal chamber of the FIG. 3 embodiment separated from the thoracic vacuum regulator.
Figure 5:
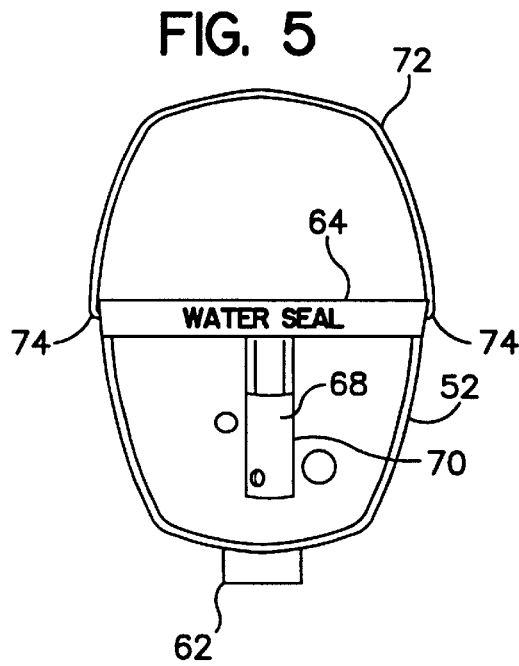
FIG. 5 is a further front view of the water seal chamber of FIG. 4.

Turning now to FIGS. 4 and 5, there are shown front views of the water seal chamber 52 that has been detached from its position shown in FIG. 3 affixed to the housing 44. In FIG. 4, the locking hanger 72 is a position against the water seal chamber 52 and in FIG. 5, the locking hanger 72 has been pivoted from the FIG. 4 position to an extended position where it can easily be affixed to a IV pole or other hanging device so as to hang the water seal chamber 52 alongside the patient as the patient is moved from one location to another within the health care facility.

The actual means of removably affixing the water seal chamber 52 to the housing 44 can be by a variety of mechanisms. As can be seen in FIG. 4, there may be a pair of elongated flanges 76 formed in the upper surface 64 of the water seal chamber 52 and which mate with corresponding flanges (not shown) formed on the lower surface 66 of the thoracic vacuum regulator 50 so that the water seal chamber 52 can simply be slid in the forward direction to separate the water seal chamber 52 from the housing 44 and break the fluid interconnection with the thoracic vacuum regulator 50.

Figure 6:
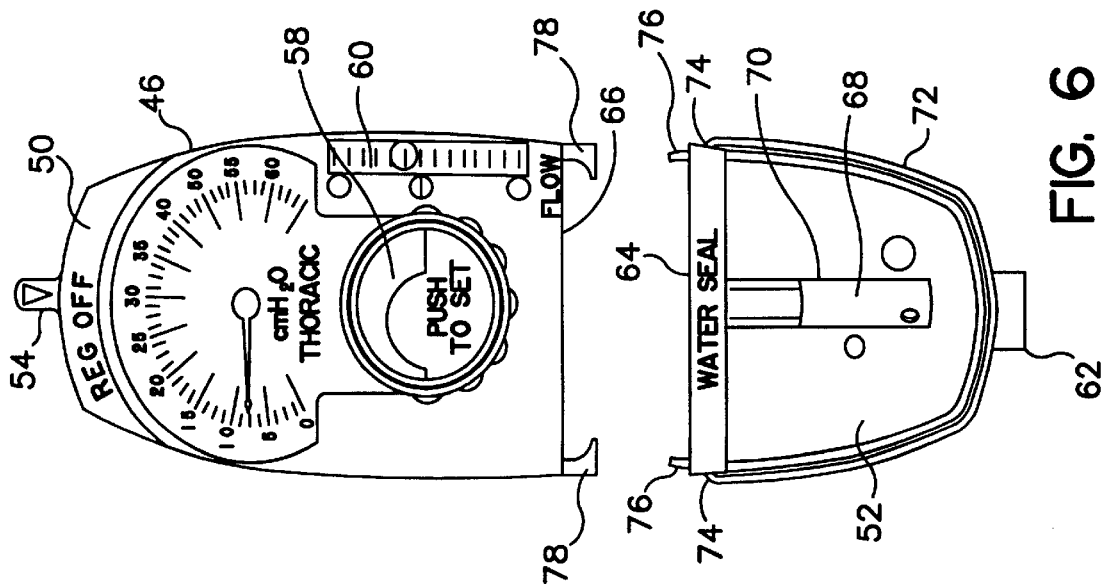
FIG. 6 is a front, exploded view of the embodiment of FIG. 3.

Turning now to FIG. 6, there is shown a front, exploded view of the embodiment of FIGS. 3–5 and providing a better view of the elongated flanges 76 formed on the upper surface 64 of the water seal chamber 52 and which slidingly mate with the dovetailed slide rails 78 formed on the lower surface 66 of the thoracic vacuum regulator 50. As such, it can be seen that by a simple sliding motion, the water seal chamber 52 can be attached and detached from the housing 44 and therefore, the thoracic vacuum regulator 10.

Figure 7C:
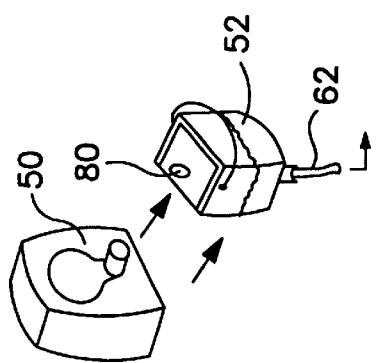
FIGS. 7A–7D are schematic views of the embodiment of FIG. 3 illustrating its use.
Figure 7D:
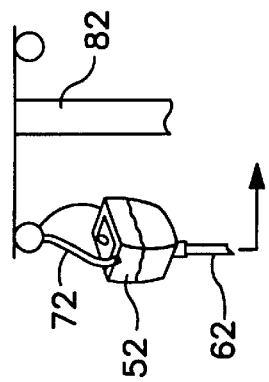
Figure 7A:
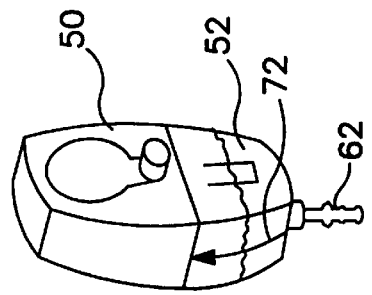
Figure 7B:
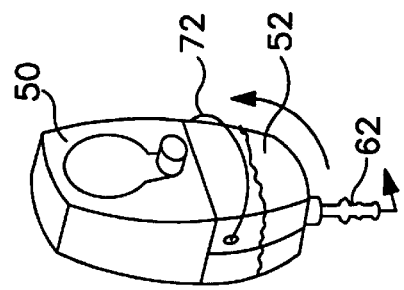

Finally, turning to FIGS. 7A–7D, there are a series of schematic views that exemplify the manner in such the present invention can be used. Thus, in FIG. 7A, there is a view of the combined vacuum regulator/water seal chamber affixed together and such apparatus would normally be located at eye level of the caregiver connected to a wall outlet for vacuum. In FIG. 7B, the locking handle 72 has been pivoted forwardly preparatory to removing the water seal chamber 52 from the thoracic vacuum regulator 50. In FIG. 7C, the locking hanger 72 has been pulled forwardly by the user and the dovetail engagement between the thoracic vacuum regulator 50 and the water seal chamber 52 has been separated. In this Figure, there can also be seen the outlet 80 for the water seal chamber 52. In FIG. 7D, the water seal chamber 52 has been hung on an IV pole 82 and therefore can be carried along with the patient as that patient is transported from one location to another and still retain the important function of the water seal during the patient's travel easily and without complicated procedures required of the caregiver.

Those skilled in the art will readily recognize numerous adaptations and modifications which can be made to the thoracic drainage system and method of use thereof which will result in an improved system and method yet all of which will fall within the scope and spirit of the present invention as defined in the following claims. Accordingly, the invention is to be limited only by the following claims and their equivalents.

We claim:

1. A thoracic drainage system for withdrawing liquids from a cavity of a medical patient, said thoracic drainage system comprising a disposable collection chamber, a vacuum regulator adapted to be connected to a source of vacuum to provide a level of vacuum to the collection chamber within a predetermined range, the vacuum regulator comprising a housing having a regulator knob affixed to the housing to set the desired level of vacuum established by the vacuum regulator and a regulator gauge located in said housing to visually determine the level of vacuum set by the vacuum regulator, a tube having a distal end adapted to be located in the cavity of a patient to withdraw by suction liquids from a cavity, an individual, independent disposable water seal chamber having an outlet adapted to be connected to the predetermined level of vacuum of said vacuum regulator and an inlet communicating with said collection chamber, said water seal chamber comprising a molded plastic body having a quantity of liquid contained therein with the inlet located below the level of the quantity of liquid and the outlet located above the level of the quantity of liquid, said water seal chamber being readably removable from the thoracic drainage system to be physically separated from the disposable collection chamber and the vacuum regulator.

2. A thoracic drainage system as defined in claim 1 wherein said predetermined quantity of liquid is a pre-filled quantity of water.

3. A thoracic drainage system as defined in claim 2 wherein said inlet and said outlet include removable sealing caps that prevent the water from spilling from the water seal chamber.

4. A thoracic drainage system as defined in claim 1 wherein said water seal chamber is removably affixed to said thoracic vacuum regulator.

5. A thoracic drainage system as defined in claim 4 wherein said water seal chamber is removably affixed to said thoracic vacuum regulator by means of an elongated flange on said water seal chamber that slidingly interfits into a mating elongated flange on said thoracic vacuum regulator.

6. A thoracic drainage system as defined in claim 4 wherein said water seal chamber has a locking hanger attached thereto to enable said water seal chamber to be suspended by said locking hanger.

7. A thoracic drainage system as defined in claim 6 wherein said locking hanger is pivotally affixed to said water seal chamber.

8. A disposable water seal for a thoracic drainage system, said disposable water seal comprising a plastic housing forming an enclosed chamber, said plastic housing having sides, a bottom and a cover, an inlet and an outlet communicating with said chamber through said cover, a quantity of liquid contained within the enclosed chamber, said inlet extending downwardly to a point below the level of said liquid, and a opening in said cover for adding additional liquid to the quantity of liquid within the enclosed chamber said opening being covered with a flexible diaphragm that is pierceable by an instrument to add water to said enclosed chamber.

9. A disposable water seal for a thoracic drainage system as defined in clam 8 where in said inlet and said outlet include sealing caps to prevent the leakage of water from the enclosed chamber.

10. A combination thoracic vacuum regulator and water seal chamber comprising a housing, a thoracic vacuum regulator contained within said housing, a regulator knob affixed to the housing to set the desired level of vacuum established by the vacuum regulator, a regulator gauge located in said housing to visually determine the level of vacuum set by the vacuum regulator, and a disposable water seal chamber removable affixed to said housing, said water seal chamber containing a predetermined quantity of liquid, an inlet located below the level of the liquid and an outlet located above the level of the liquid, and a means to removably affix said water seal chamber to said thoracic vacuum regulator.

11. A combination thoracic vacuum regulator and water seal chamber as defined in claim 10 wherein said water seal chamber includes a locking hanger pivotally affixed thereto.

12. A combination thoracic vacuum regulator and water seal chamber as defined in claim 11 wherein said water seal chamber has an upper surface having an outlet opening formed therein and said thoracic vacuum regulator has a lower surface having an inlet opening therein.

13. A combination thoracic vacuum regulator and water seal chamber as defined in claim 12 having an outlet opening of said water seal chamber and an inlet opening of said thoracic vacuum regulator are in alignment when said water seal chamber is affixed to said thoracic vacuum regulator.

14. A combination thoracic vacuum regulator and water seal chamber as defined in claim 12 having means to removably affix said water seal chamber to said thoracic vacuum regulator comprises an elongated flange on said water seal and an elongated flange on said regulator, said elongate flanges adapted to slidingly interconnect together.

15. A method of removing fluids from an internal cavity of a patient by means of a thoracic drainage system, said method comprising the steps of:
   providing a housing having incorporated therein, a vacuum regulator for providing a level of vacuum to an internal cavity of a patient, a regulator knob to set the desired level of vacuum established by the regulator, a regulator gauge to visually determine the level of vacuum set by the vacuum regulator and a water seal chamber for preventing ambient air from entering a patient cavity,
   separating the water seal chamber from the housing for use with a patient in order to continue the function of a water seal for protection to a patient while a patient is being transported from one location to another.

16. A method as defined in claim 15 wherein said step of separating the water seal chamber from the housing comprises providing a mobile device adapted to be transported along with a patient and affixing the separated water seal chamber to the mobile device for the transportation of a patient.

17. A method as defined in claim 16 wherein said step of separating the water seal chamber from the housing comprises providing a hanger on the water seal chamber and manually affixing the hanger to the mobile device to affix the water seal chamber suspended from the mobile device.

18. A method as defined in claim 15 wherein said step of separating the water seal chamber from the housing comprises disengaging the water seal chamber by a sliding interfitting between the water seal chamber and the housing.

19. A method as defined in claim 15 wherein said step of separating the water seal chamber from the housing comprises providing mutually interengaging flanges on the water seal chamber and the housing that are readily separated.

* * * * *